(12) United States Patent
Axelsson et al.

(10) Patent No.: US 7,699,824 B2
(45) Date of Patent: Apr. 20, 2010

(54) ADAPTER, LID AND CONNECTOR FOR OSTOMY BAGS

(75) Inventors: Robert Axelsson, Granna (SE); Thomas Arnerdal, Bankeryd (SE); Johan Rinman, Aneby (SE); Anette Johnsson, Jönköping (SE)

(73) Assignee: Ostomycure AS, Oslo (NO)

( * ) Notice: Subject to any disclaimer, the term of this patent is extended or adjusted under 35 U.S.C. 154(b) by 151 days.

(21) Appl. No.: 11/740,783

(22) Filed: Apr. 26, 2007

(65) Prior Publication Data

US 2007/0244452 A1 Oct. 18, 2007

Related U.S. Application Data

(63) Continuation of application No. PCT/IB2005/053504, filed on Oct. 26, 2005.

(30) Foreign Application Priority Data

Oct. 27, 2004 (EP) .................................. 04077965

(51) Int. Cl.
*A61F 5/44* (2006.01)
(52) U.S. Cl. .................. 604/338; 604/317; 604/323; 604/324; 604/326; 604/327; 604/331; 604/332; 604/333; 604/337; 604/339; 604/341; 604/350; 604/355

(58) Field of Classification Search .......... 604/337–339
See application file for complete search history.

(56) References Cited

U.S. PATENT DOCUMENTS

| 4,121,589 | A | | 10/1978 | McDonnell | ................. 128/283 |
| 4,721,508 | A | * | 1/1988 | Burton | ........................ 604/338 |
| 4,804,375 | A | * | 2/1989 | Robertson | .................... 604/323 |
| 5,139,492 | A | * | 8/1992 | Leise et al. | .................. 604/339 |
| 6,033,390 | A | * | 3/2000 | von Dyck | .................... 604/332 |

FOREIGN PATENT DOCUMENTS

WO WO 00/62722 10/2000
WO WO 2004/108016 A1 * 12/2004

\* cited by examiner

*Primary Examiner*—Tatyana Zalukaeva
*Assistant Examiner*—Ilya Y Treyger
(74) *Attorney, Agent, or Firm*—Winston & Strawn LLP

(57) ABSTRACT

The invention relates to an adapter attached to a human or animal body at a stoma, a detachable lid on the adapter, and a connector for connecting an ostomy bag to the adapter. The adapter includes a protruding section extending from the stoma, and a member for mounting a detachable lid onto the end of the protruding section. The adapter and lid are arranged such that the lid can be slid onto and off the adapter in a direction relatively perpendicular to the axis of the protruding section of the adapter. The connector is arranged to connect the ostomy bag to the adapter and to slide the lid off the adapter. In this way, there is no risk of odors or waste leaking from the adapter or the ostomy bag while the bag is being connected to the adapter.

23 Claims, 5 Drawing Sheets

ADAPTER, LID AND CONNECTOR FOR OSTOMY BAGS

CROSS-REFERENCE TO RELATED APPLICATIONS

This application is a continuation of International application PCT/IB2005/053504 filed Oct. 26, 2005, the entire content of which is expressly incorporated herein by reference thereto.

BACKGROUND

The invention relates to an adapter attached to a human or animal body at a stoma, a detachable lid on the adapter, and a connector for connecting an ostomy bag to the adapter. The adapter is of the kind which comprises a protruding section extending from the stoma, and mounting means for mounting a detachable lid onto the end of the protruding section.

The invention also relates to a method of connecting an ostomy bag to an adapter at a stoma and a method of removing an ostomy bag from an adapter at a stoma. A lid exchanger for replacing the lid on the adapter with a replacement lid and a method of using the lid exchanger are also provided.

Many diseases such as e.g. Crohn's disease, ulcerative colitis, intestinal cancer and adenomatous polyposis or bladder cancer require removal of all or part of the intestines or bladder. When the intestines or the bladder are removed, the bodily wastes are expelled through a new surgical opening in the abdominal wall. The surgery to create the new opening, the stoma, is called ostomy.

Once the stoma has been created, an external bag, typically called an ostomy bag, is connected to the stoma in order to collect bodily waste. When the ostomy bag is filled, it is removed and emptied. Some ostomy bags can be cleaned and reused while other ostomy bags are discarded and replaced with new ones.

The ostomy bag can be connected directly to the stoma by attaching it to the skin with an adhesive substance. However, typically the ostomy bag is detachably connected to an adapter mounted at the stoma. The adapter is usually attached to the body at the stoma with an adhesive wafer. This means that the bag can be emptied or replaced more frequently without needing to disrupt the adhesive contact at the body.

New adapters however have recently been developed which can be implanted into the body at the stoma. See for example European patent application 1632201. These "implants" become an integrated part of the body which creates a stronger and more robust connection between the body and the adapter. In addition, it is not necessary to use an adhesive substance to attach the adapter to the body.

There are many different types of systems which allow ostomy bags to be connected to an adapter at a stoma. One example of such a system is provided by WO 03/013404. WO 03/013404 provides a coupling for connecting an ostomy bag to an adapter having a tubular protruding section. The adapter could either be attached to the skin around the stoma with an adhesive or the adapter could be surgically implanted at the stoma. The coupling according to WO 03/013404 clamps onto the tubular protruding section of the adapter when the user presses two co-axial discs together. The user releases the bag from the adapter by pulling the two co-axial discs away from each other. The two co-axial discs are located on the inside surface of the ostomy bag.

However, the big disadvantage with currently available systems is that during the exchange procedure, both the adapter and the bag are open. This means that there is a risk of odors or waste leaking from the stoma and/or the bag. This makes exchanging the ostomy bag a rather unpleasant task.

SUMMARY OF THE INVENTION

A first aspect of the current invention is to provide an adapter, a detachable lid, and a connector as mentioned in the opening paragraph in order to ensure that no waste or odors are released from the adapter and/or the ostomy bag while the ostomy bag is being exchanged or emptied.

A second aspect of the current invention is to provide an adapter, a detachable lid and a connector as mentioned in the opening paragraph which are easy to operate.

A third aspect of the current invention is to provide a connector as mentioned in the opening paragraph which replaces the detachable lid on the adapter when the ostomy bag is exchanged.

A fourth aspect of the current invention is to provide a method of removing an ostomy bag from an adapter at a stoma and a method of connecting an ostomy bag to an adapter at a stoma which ensure that no waste or odors are released during the removing and the connecting respectively.

The new and unique way in which the adapter according to the current invention fulfills the above mentioned aspects is that the mounting means are arranged such that the detachable lid is mounted onto and removed from the end of the protruding section by sliding the detachable lid in a direction relatively perpendicular to the axis of the protruding section. In this way, the adapter can be inserted into a connector which can slide the lid off the adapter once the bag is connected to the adapter. The connector can then slide the lid onto the adapter again, when the bag is to be removed from the adapter. This means that the only time that the adapter is open is when the ostomy bag is connected to the adapter. This ensures that there is no leakage from the adapter and that no odors are released during the exchange or the emptying of the bag.

In an advantageous embodiment, the mounting means can comprise grooves or ridges formed complementary to ridges or grooves respectively on the detachable lid, the grooves or ridges running perpendicular to the axis of the tubular section. This is a simple way of allowing the detachable lid to be held in place during normal use, but easily slid off the end of the adapter when the bag is to be exchanged.

In an especially advantageous embodiment, the adapter can be an implant. This allows the adapter to become an integrated part of the body. This also allows the adapter to withstand higher forces and allows the adapter to be used with the lid on for longer periods of time. The traditional adapter which is attached to the body with an adhesive can not withstand much back pressure before the adhesive releases from the body.

The invention further comprises a detachable lid as mentioned in the opening paragraph which is arranged to be mounted onto and removed from the end of a protruding section of an adapter by sliding the lid substantially perpendicularly to the axis of the protruding section. This allows it to work together with the adapter according to the invention.

In an advantageous embodiment, the lid can further comprise ridges or grooves which are formed complementary to grooves or ridges respectively on the adapter which run perpendicular to the axis of the protruding section of the adapter. This is a simple way to make the lid slideable with respect to the adapter.

The detachable lid can further comprise a first seal which prevents waste and odors from escaping the adapter. The lid can furthermore be made gas permeable to ensure that high pressure is not built up behind the adapter. In order to remove odors from the gases passing through the lid, the lid can also comprise an odor filter.

The invention further comprises a connector as mentioned in the opening paragraph which comprises: a first part, a second part arranged such that it is displaceable with respect to the first part, a first through going opening in the first part, arranged such that the protruding section of the adapter is insertable into the first opening, a first recess in the second part to accept the detachable lid mounted on the adapter, a second through going opening in the second part beside the recess, and sliding means to slide the second part relative to the first part, from a first position where the first recess is aligned with the first opening, to a second position where the second opening is aligned with the first opening. In this way, a connector is provided which can connect an ostomy bag to an adapter with a detachable lid and disconnect an ostomy bag from an adapter with a detachable lid without any waste or odor leakage.

The connector can be integrated directly into the ostomy bag. In an advantageous embodiment the first part can be attached to the inside surface of the ostomy bag. In this way, the connector and all the waste remain inside the bag. In addition there is nothing on the outside of the bag which can snag on clothing or other objects.

In order to make the connector easier to operate, the connector can further comprise a first tab on the first part and a second and third tab on the second part, where in the first position the second tab is substantially aligned with the first tab and in the second position the third tab is substantially aligned with the first tab. In this way, the connector can be moved from the first position to the second position by squeezing the first tab and the third tab together. The connector can be moved from the second position to the first position by squeezing the first tab and the second tab together.

The connector can further comprise a second seal around the second opening which prevents waste or odor leakage when the bag is connected to the adapter. The connector can furthermore be arranged such that one surface of a first seal in the detachable lid and one surface of the second seal lie on a common plane when the adapter is inserted into the connector. In this way, no waste or odor leakage occurs during connection and disconnection of the bag from the adapter.

To hold the ostomy bag and the adapter together while the bag is being filled, the connector can further comprise ridges or grooves on the second part of the connector which engage with grooves or ridges respectively on the adapter in the second position of the connector.

The connector can further comprise first alignment means at the first recess corresponding to second alignment means at the lid of the adapter. In this way it is ensured that the adapter is inserted properly into the connector. Proper alignment ensures that it is possible for the connector to easily slide the lid off the adapter.

In order to exchange the lid at the same time as the bag is being exchanged, the connector can further comprise a second recess in the second part beside the second opening and a replacement detachable lid arranged in the second recess, the second recess being placed on the opposite side of the second opening as the first recess.

If the connector does not have means for replacing the lid, a lid exchanger can be used to exchange the lid. According to the invention, such a lid exchanger comprises: a first part, a second part arranged such that it is displaceable with respect to the first part, a first through going opening in the first part arranged such that the protruding section of the adapter is insertable into the first opening, a first recess in the second part to accept the detachable lid, a second recess in the second part beside the first recess, a replacement detachable lid arranged in the second recess, and sliding means to slide the second part relative to the first part, from a first position where the first recess is aligned with the first opening to a second position where the second recess is aligned with the first opening. In this way, it is possible to insert an adapter closed by an old lid into the lid exchanger, activate the lid exchanger and remove the adapter from the lid exchanger with a new lid.

BRIEF DESCRIPTION OF THE DRAWINGS

The invention will be explained in greater detail below where further advantageous properties and example embodiments are described with reference to the drawings, in which.

DETAILED DESCRIPTION OF THE PREFERRED EMBODIMENTS

Figure 1:
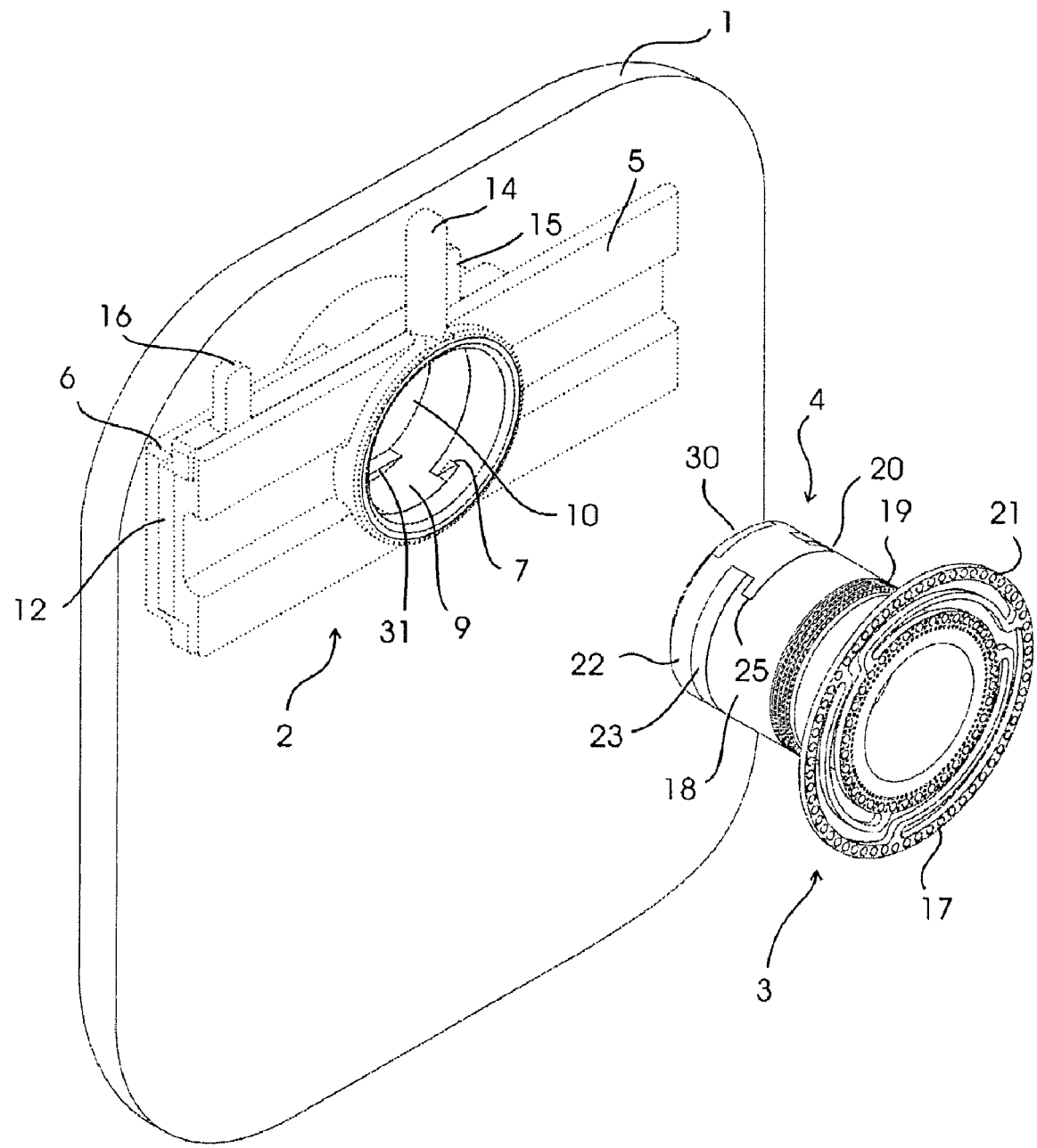
FIG. 1 is a schematic representation seen in perspective of an adapter, a detachable lid, and a connector according to the invention, where the connector is mounted inside an ostomy bag.
Figure 2:
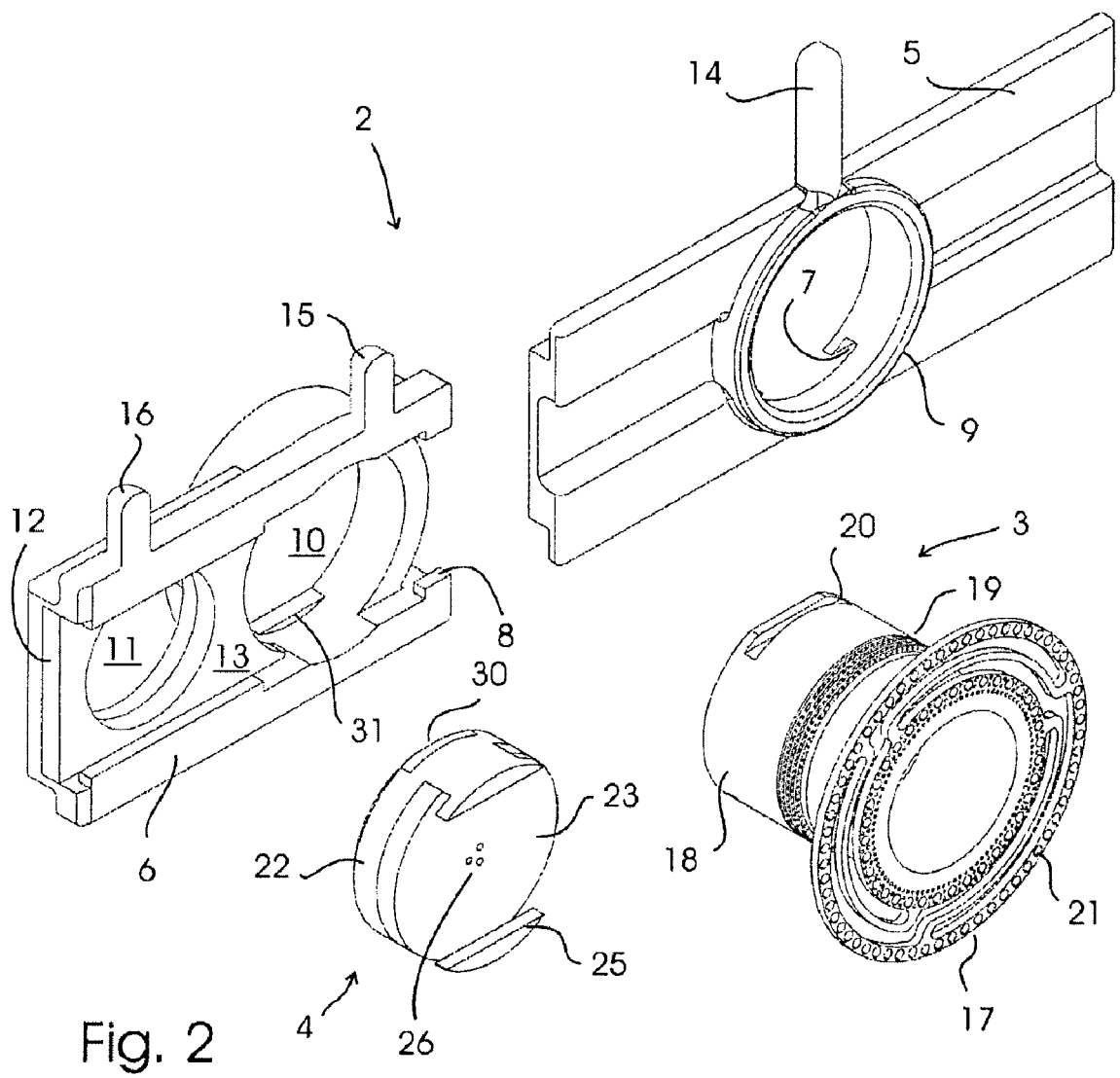
FIG. 2 shows an exploded view of the same, without the ostomy bag.

The main components shown in FIGS. 1 and 2 are an ostomy bag 1, a connector 2, an adapter 3, and a detachable lid 4 mounted on the adapter 3. The connector 2 is attached to the ostomy bag 1 on the inside of the bag. The connector 2 is therefore shown using dotted lines.

The connector comprises a first part 5 and a second part 6. The first part 5 and the second part 6 are connected to each other with sliding means which allows the second part 6 to slide sideways with respect to the first part 5. This is achieved in that the first part is formed with a groove 7 and the second part is formed with a complementary ridge 8 which fits inside the groove 7 on the first part. In this way, the first part and second part are held securely together while simultaneously allowing the second part to slide side to side with respect to the first part.

The first part 5 further comprises a first through going opening 9. The second part 6 further comprises a first recess 10 and a second through going opening 11. A seal 12 with a flat surface 13 is formed around the second opening 11. The seal 12 is firmly connected to the second part thereby preventing it from shifting sideways when the second part is slid with respect to the first part.

A first tab 14 is formed on the first part. A second 15 and third tab 16 are mounted on the second part. The tabs are used to slide the second part 6 sideways relative to the first part 5. The first tab 14 is slightly higher than the second 15 and third 16 tabs. This makes it easy for the user to distinguish between the first tab and the second and third tabs.

The connector has two main positions. In the connector's first position, the first through going opening 9 in the first part is aligned with the first recess 10. In the connector's second position, the first opening 9 is aligned with the second through going opening 11 in the second part.

In the first position of the connector, the first tab 14 is roughly aligned with the second tab 15. The third tab 16 is at a distance to the left (as seen in the FIG.) from the first tab 14. To slide the connector into the second position, the user applies pressure to the first tab 14 and the third tab 16 in order to press the two tabs together. This can be achieved by squeezing the two tabs together using the thumb and the forefinger. Since the second tab 15 and the first tab 14 are roughly aligned, the user won't be confused as to which tabs he or she should squeeze together. This is important because the connector in the current embodiment is inside the bag and the user can't see connector.

Once the connector is in the second position, the third tab 16 and the first tab 14 will be roughly aligned. To slide the connector into the first position, pressure is applied to the first 14 and second 16 tabs. Again since the first tab 14 and the third tab 16 are roughly aligned, the user won't be confused as to which tabs he or she should apply pressure to.

Another advantage of the tab setup, is that since the user applies pressure between the two tabs, no force is transmitted to the adapter. This reduces the risk of injuries to the body around the adapter. In many current systems, the user has to force the connector off the adapter. This applies large stresses to the connection between the adapter and the body.

In the current embodiment, the first part 5 of the connector is attached to the inside surface of the ostomy bag 1. This ensures that all the waste remains inside the bag, both while the bag is connected to the adapter and once it is removed. In another embodiment, it could be imagined that the connector is attached to the outside of the bag. In this case, the second part 6 of the connector would be connected to the outside surface of the bag.

The adapter 3 in the current example is an implant and is surgically implanted into the body of the user at the stoma. In effect, the adapter forms the stoma. The adapter comprises a radial flange 17, a tubular protruding section 18, a set of circumferential ribs 19, and mounting means 20. The radial flange is surgically implanted into the abdominal wall. The holes 21 in the radial flange 17 permit tissue to grow through the flange 17, thereby ensuring a strong and robust connection between the body and the adapter. The circumferential ribs 19 in the protruding section of the adapter serve to promote firm mechanical securing of the protruding section to the surrounding tissue. Furthermore the ribs impede downgrowth of the epithelium. More details of the implant, as shown in the FIGS., can be found in the inventor's European Patent application with application number 04077475.4 (not yet published).

Once the adapter is implanted into the body, only the end of the tubular protruding section 18 extends out of the body of the user. Mounting means 20, for mounting a detachable lid 4 are arranged at the end of the protruding section. In the current example, the mounting means comprises two grooves 20 in the end of the protruding section. The grooves 20 run perpendicular to the longitudinal axis of the protruding section 18. This allows the lid to be slid on and off the adapter in a direction which is perpendicular to the axis of the protruding section.

Figure 3:
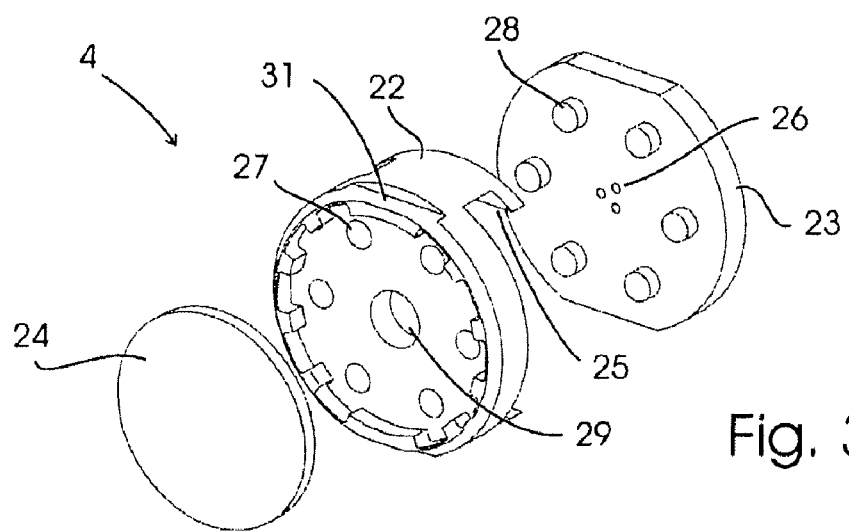
FIG. 3 shows an exploded view of the lid.

The lid 4 shown in FIGS. 1, 2 and 3 has three components: a rigid plastic part 22, a seal 23, and a carbon filter 24 (can only be seen in FIG. 3). The rigid plastic part 22 is formed with two rails 25 which engage with the grooves 20 on the adapter when the lid is mounted on the adapter. The rails allow the lid to be slid on and off the adapter in a direction which is perpendicular to the axis of the protruding section.

The seal 23 is made from a sealing material, such as rubber, and has three small holes 26 which go through the seal. This allows gases to pass through the lid. The carbon filter 24, on the outside of the lid, filters the gasses coming through the lid in order to remove any odors.

In FIG. 3, one can see a number of through holes 27 in the rigid plastic part of the lid which engage with protrusions 28 on the first seal. These holes and protrusions hold the seal 23 in place. A larger through hole 29 allows the gasses coming through the small holes 26 in the first seal to get to the carbon filter 24.

The lid also has alignment means 30 which match corresponding alignment means 31 in the first recess 10 of the second part 6 of the connector 2. The first alignment means 31 in the first recess comprise two raised ridges on the bottom surface of the recess. The second alignment means 30 on the lid comprises two flattened parts on the outer periphery of the rigid plastic part. When the adapter with the lid is inserted into the connector, the two alignment means engage each other. This ensures that the adapter is inserted into the connector in the correct orientation.

The alignment means could be formed in many other ways as well. For example, the alignment means in the recess could be a groove running along the bottom of the recess and the alignment means on the lid could be a ridge which corresponds to the groove in the recess. In addition, the adapter shown in the FIGS. has a circular cross section. In other embodiments, the adapter could have a non-circular cross section, for example elliptical. This would ensure that the adapter and the connector are properly aligned when the adapter is inserted in the connector.

The lid and the adapter can also have a locking arrangement which secures the lid on the adapter during normal use and prevents it from being slid off. This is not shown in the FIGS. For example, an outer lid can be placed over the lid and adapter during normal use. Before connecting the adapter to the bag, the outer lid would be removed. After disconnecting the bag, the outer lid would be mounted again.

Figure 4:
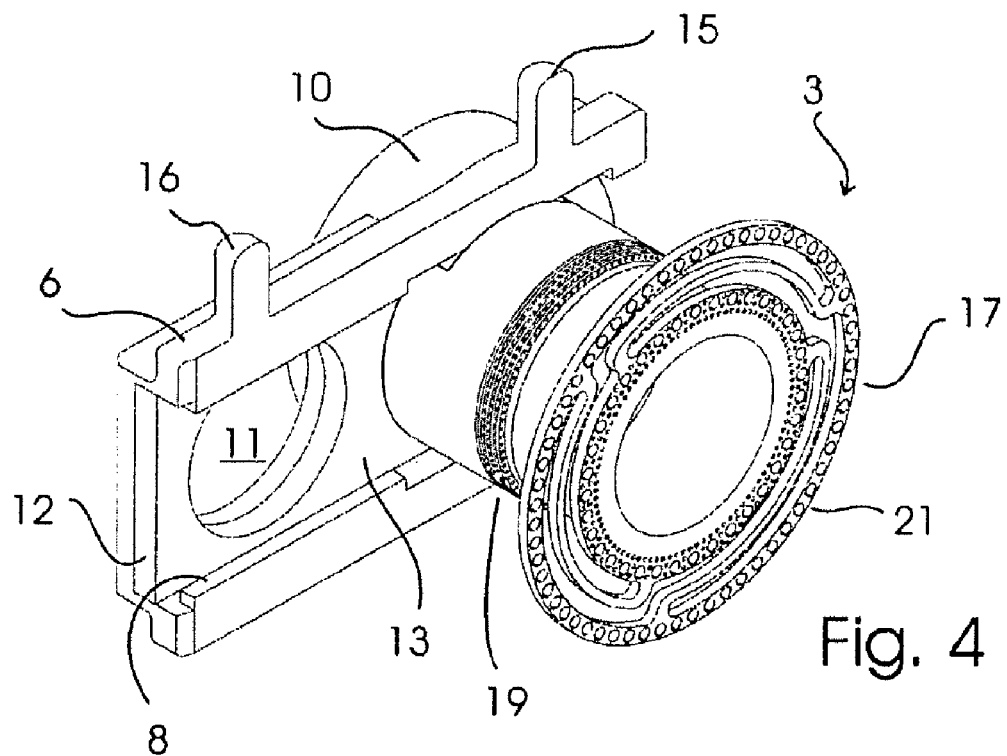
FIG. 4 shows an enlarged view of the adapter and lid inserted into a part of the connector, in a first position.
Figure 5:
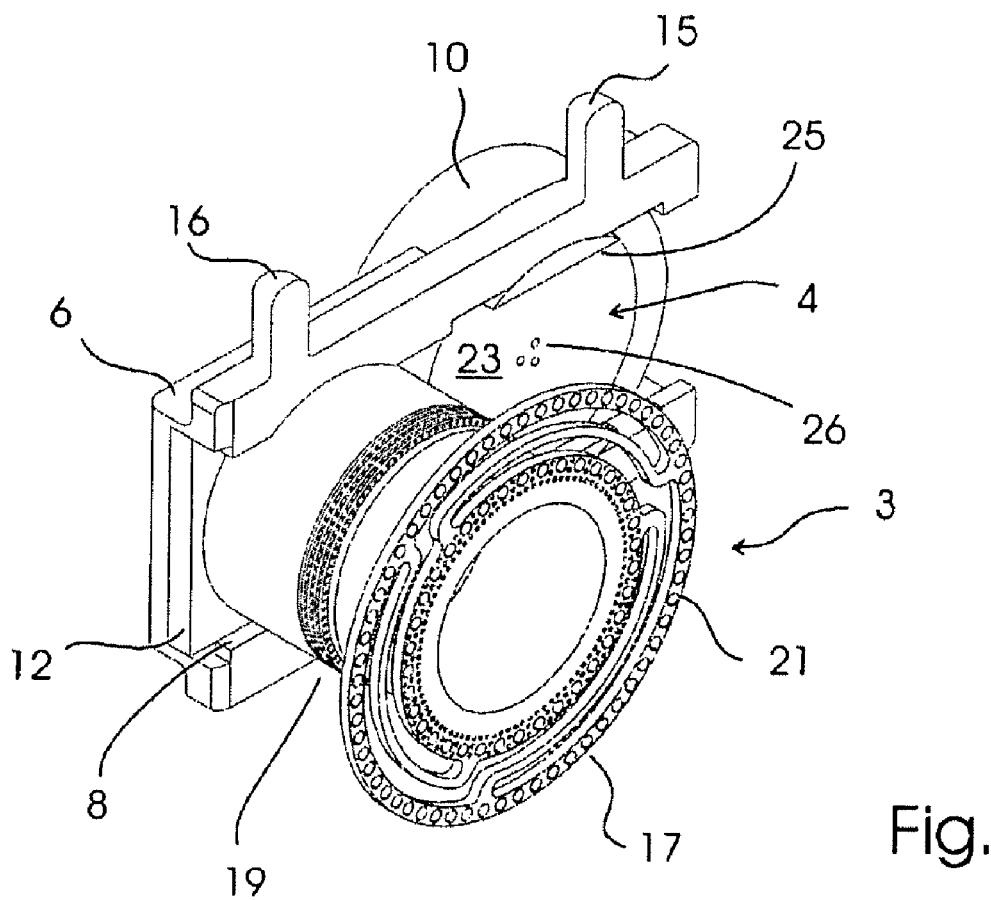
FIG. 5 shows the same, in a second position

FIGS. 4 and 5 show two of the steps of connecting the ostomy bag equipped with the connector to the adapter. So that the inner workings of the adapter and connector can be seen, the ostomy bag and the first part of the connector are not shown. FIG. 4 shows the connector in its first position and FIG. 5 shows the connector in its second position. It should be noted that the first through going opening 9 in the first part 5 would be aligned with the protruding section 18 of the adapter 3 if the first part where shown in FIGS. 4 and 5.

In FIG. 4 the adapter has just been inserted into the first through going opening in the first part. As can be seen, the lid 4 fits into the first recess 10 in the second part of the connector. In FIG. 5, the second part has been slid to the right (according to the FIG.) with respect to the adapter and the first part of the connector. As can be seen, by sliding the second part to the right, the protruding section of the adapter and the first opening in the first part of the connector are brought inline with the second opening in the second part of the connector. In this case, waste can be expelled through the protruding section of the adapter and be collected in the ostomy bag.

While the connector is in the second position, the lid is held in the first recess. Also, while the connector is in the second position, the ridges of the second part of the connector engage with the grooves at the end of the adapter, thereby locking the adapter to the connector.

Furthermore, it can be seen that the top surface 13 of the seal 12 in the second part of the lid, is aligned with the top surface of the second seal 23, thereby allowing the end of the protruding section of the adapter to slide on a common surface between the first position and the second position. In this way, it is possible to ensure that no leakage occurs while the connector is being moved from the first position to the second position.

When the user is finished with filling the bag, the user applies pressure between the second tab 15 and the first tab 14. This causes the second part to slide to the left (according to the FIG) with respect to the first part of the connector and the adapter. By sliding the second part to the left, the lid is slid onto the protruding section of the adapter, the second opening in the second part of the connector is closed, and the connector unlocks the adapter which allows the user to remove the adapter from the connector. The adapter is now closed again with the old lid.

Figure 6:
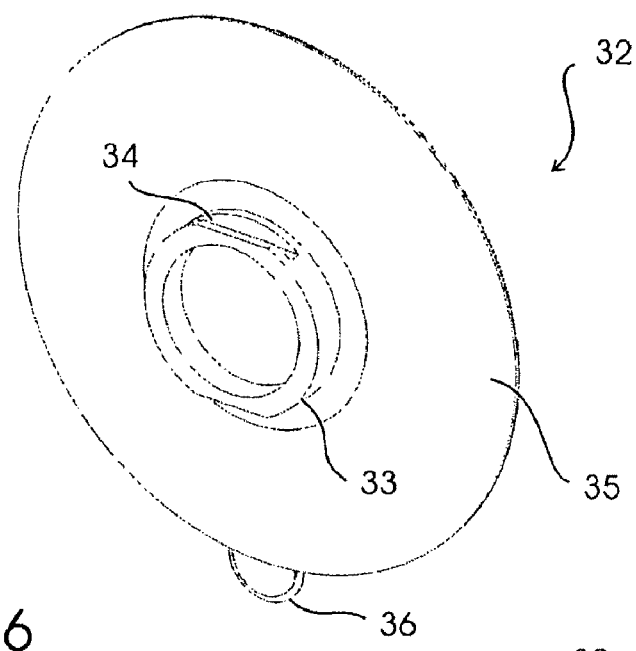
FIG. 6 shows a second embodiment of an adapter according to the invention.

FIG. 6 shows a second embodiment 32 of an adapter according to the invention. This adapter 32 is designed to be attached to the body around a traditional stoma using adhesive tape. The adapter comprises a protruding section 33, mounting means 34, an adhesive wafer 35 rigidly connected to the base of the protruding section, and a peel off cover 36 on the adhesive wafer. The mounting means 34 on this adapter are identical to the mounting means on the adapter 3 described in FIGS. 1 and 2. This means that a lid identical to the one shown in FIGS. 1-3 and described above can be attached to this adapter in the same way as was described above.

The adhesive wafer is attached around the stoma in the same way as a traditional connector for an ostomy bag is attached to the stoma. Once the adapter is connected to the body, an ostomy bag with a connector as shown in FIGS. 1 and 2 can be attached to the adapter in the same way as described above. This allows people with a traditional stoma to use a bag with a connector according to the current invention, thereby eliminating the risks of leakage during the bag exchange process.

Since the adapter is only attached to the skin via the adhesive wafer, the bond is not as strong as with an implant. Therefore, the user should not go for too long with the lid on the adapter. This could cause a pressure to be applied to the adapter which could cause the adhesive to release. It would therefore be recommended to use a bag connected to this type of adapter at all times. In this case, the bag can be formed with a gas permeable opening and a carbon filter in order to let gases escape from the bag.

Figure 7:
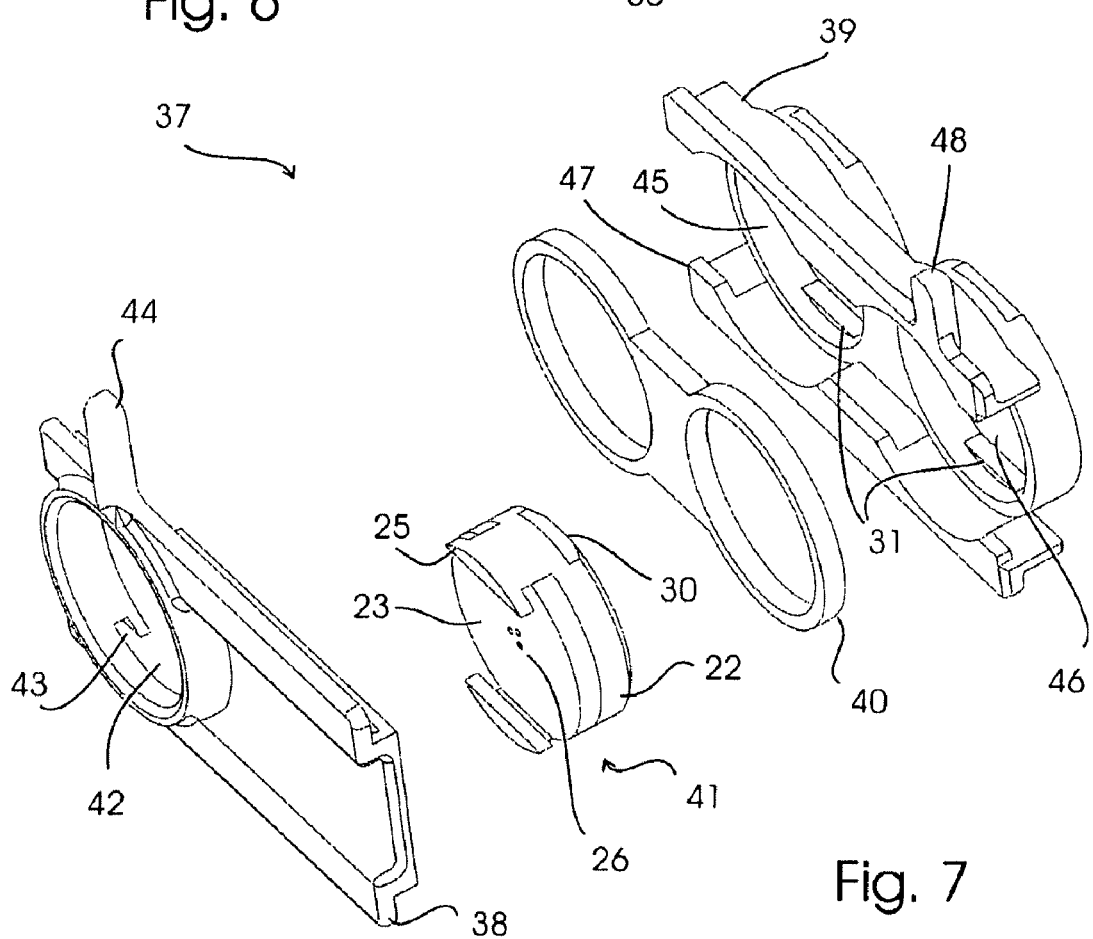
FIG. 7 shows an exploded schematic representation of a lid exchanger according to the invention.

After a certain amount of time, the user will want to exchange the lid on the adapter with a new one. There are many reasons for this, for example the lid can accumulate waste material, the seal can get worn, the holes in the seal be plugged up, etc. A lid exchanger 37 as shown in FIG. 7 can be used for this purpose.

The lid exchanger 37 is very similar in principle to the connector 2 as described above. The lid exchanger 37 comprises a first part 38, a second part 39, a seal 40, and a replacement lid 41. The replacement lid is identical to the one described above and therefore won't be described further here.

The first part 38 comprises a first opening 42, grooves 43 and a first tab 44. The second part 39 comprises a first recess 45, a second recess 46, ridges 47, and a second tab 48. The first and second parts are slideably connected together via the grooves 43 and the ridges 47. The replacement lid 41 is arranged inside the second recess 46.

The lid exchanger has two main positions, a first position where the first opening is aligned with the first recess and a second position where the first opening is aligned with the second recess.

When it is desired to exchange the lid, the adapter with the old lid is inserted into first opening of the lid exchanger when it is in a first position. The lid is therefore inserted into the first recess. The user then applies pressure between the first 44 and second 48 tabs and slides the second part relative to the first part. In this way, the first lid is slid off the adapter and the replacement lid is slid onto the end of the adapter. Once the lid exchanger is in its second position, the adapter can be removed from the lid exchanger. The old lid remains in the lid exchanger which can now be discarded and the replacement lid is mounted on the end of the adapter.

Figure 8:
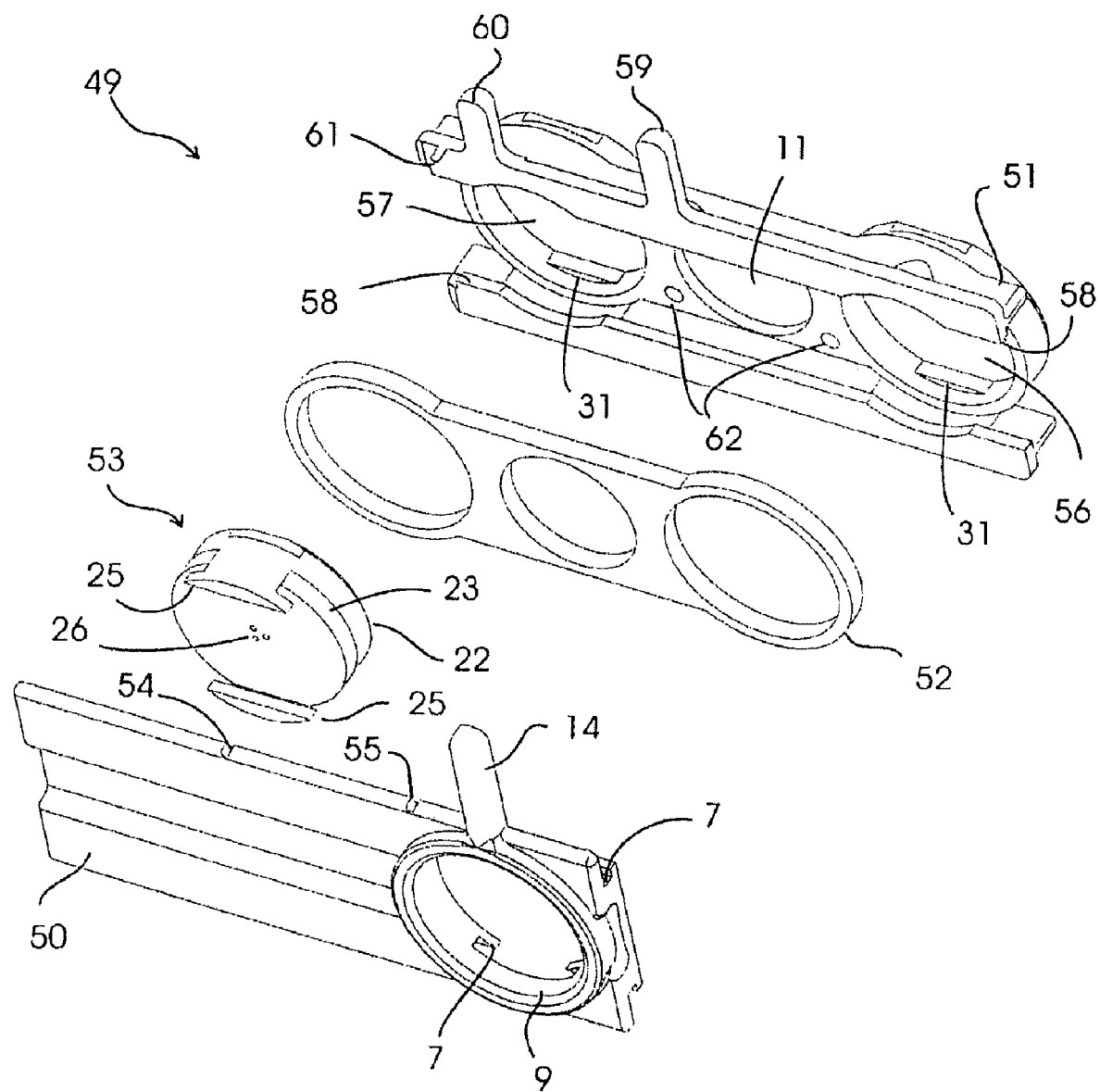
FIG. 8 shows an exploded schematic representation of a second embodiment of a connector according to the invention.

FIG. 8 shows a second embodiment 49 of a connector according to the invention. The connector 49 is similar to the connector 2 as described above and the same reference numerals will therefore be used to describe similar parts. The second embodiment 49 of the connector however, exchanges the old lid with a replacement lid after the bag has been filled.

The connector 49 comprises a first part 50, a second part 51, a seal 52 and a replacement lid 53. The replacement lid 53 is identical to the lid 4 described above and it will therefore not be described further here. The first part 50 has a first opening 9, grooves 7, a first tab 14, and two indentations 54,55 on the top of the first part. The second part 51 comprises a first recess 56, a second recess 57, a second opening 11, ridges 58, a second 59 and third 60 tab, and a protrusion 61. As in the previous example of a connector 2, the recesses have alignment means 31. The new lid 53 is arranged inside the second recess 57. The seal 52 fits into the second part 51 as was the case in the previously described connector 2. The seal is made from a flat sealing material.

Circular protrusions (hidden in the FIG) on the seal 52 engage with holes 62 in the second part in order to hold the seal in place.

The connector 49 has three main positions. In the first position, the first opening 9 is aligned with the first recess 56. In the second position, the first opening 9 is aligned with the second opening 11. In the third position, the first opening 9 is aligned with the second recess 57.

When the user desires to fill the bag, the user inserts the adapter with the old lid into the first opening. This brings the old lid into the first recess. The user then squeezes the first and second tabs together, thereby causing the second part to slide relative to the first part. The user keeps pressing until the protrusion 61 clicks into the first indentation 54 with an audible click. Waste can then be emptied from the user into the bag through the second opening. The old lid is held in the first recess.

Once the user is finished, the user applies pressure between the first tab 14 and the third tab 60. This causes the second part 51 to slide further to the right relative to the first part 50. The user continues to apply pressure until the protrusion 61 falls into the second indentation 55 in the first part with an audible click. The second opening is now closed and the replacement lid is now mounted onto the adapter. The user can then remove the adapter from the connector. The adapter now has a new lid mounted on the end of the adapter and the old lid is held in the connector inside the bag. The bag can then be discarded.

It should be obvious to the person skilled in the art that the above connector and adapter can be formed in many different ways within the scope of the invention. The above description and the FIGS. should therefore only be used as example embodiments.

For example, in the description and the drawings, the two parts of the connector are linearly displaceable with respect to each other. However, it could be imagined that the two parts are, for example, rotatably displaceable with respect to each other.

What is claimed is:

1. A combination comprising a connector for connecting an ostomy bag to an adapter for attachment to a human or animal body at a stoma, the adapter comprising a protruding section extending from the stoma, and mounting means for mounting a detachable lid onto the end of the protruding section, with the mounting means arranged such that the detachable lid is mounted onto and removed from the end of the protruding section by sliding the detachable lid in a direction relatively perpendicular to the axis of the protruding section; with the adapter having a detachable lid mounted thereon, wherein the connector comprises:
a first part,
a second part arranged such that it is displaceable with respect to the first part,
a first through going opening in the first part, arranged such that the protruding section of the adapter is insertable into the first opening,
a recess in the second part to accept the detachable lid mounted on the adapter,
a second through going opening in the second part beside the recess, and
sliding means to slide the second part relative to the first part, from a first position where the recess is aligned with the first opening, to a second position where the second opening is aligned with the first opening.

2. The combination of claim 1, wherein the detachable lid is arranged to be mounted onto and removed from the end of the protruding section of the adapter by sliding the lid substantially perpendicularly to the axis of the protruding section.

3. The combination according to claim 1 wherein the first part is attached to the inside surface of the ostomy bag.

4. The combination according to claim 1 wherein the connector further comprises a first tab on the first part, and a second and third tab on the second part, where in the first position the second tab is substantially aligned with the first tab and in the second position the third tab is substantially aligned with the first tab.

5. The combination according to claim 1 wherein the connector further comprises a second seal around the second opening.

6. The combination of claim 5, arranged for connecting an ostomy bag to an adapter that includes grooves or ridges formed complementary to ridges or grooves respectively on the detachable lid, the grooves or ridges running perpendicular to the axis of the tubular section, wherein the second seal is arranged such that one surface of the first seal and one surface of the second seal lie on a common plane when the adapter is inserted into the connector.

7. The combination according to claim 6 wherein the connector further comprises ridges or grooves on the second part which engage with grooves or ridges respectively on the adapter in the second position of the connector.

8. The combination according to claim 1 wherein the connector further comprises first alignment means at the first recess corresponding to second alignment means at the lid of the adapter.

9. The combination according to claim 1, wherein the connector further comprises a second recess in the second part beside the second opening, the second recess being, on the opposite side of the second opening with respect to the first recess.

10. The combination according to claim 9, wherein a replacement detachable lid is arranged in the second recess.

11. A combination comprising a lid exchanger for use with the combination according to claim 1, where the detachable lid is arranged to be mounted onto and removed from the end of the protruding section of the adapter by sliding the lid substantially perpendicularly to the axis of the protruding section, wherein the lid exchanger comprises:
a first part,
a second part arranged such that it is displaceable with respect to the first part,
a first through going opening in the first part, arranged such that the protruding section of the adapter is insertable into the first opening,
a first recess in the second part to accept the detachable lid,
a second recess in the second part beside the first recess,
a replacement detachable lid arranged in the second recess, and
sliding means to slide the second part relative to the first part, from a first position where the first recess is aligned with the first opening to a second position where the second recess is aligned with the first opening.

12. A method for attaching an ostomy bag with a connector to an adapter at a stoma using the combination of claim 1, which comprises:
inserting a protruding section of the adapter into a first opening in the connector, locking the adapter to the connector,
sliding a lid off the protruding section of the adapter in a direction roughly perpendicular to the axis of the protruding section, and
bringing the protruding section of the adapter and the first opening in the first part of the connector inline with a second opening in the connector.

13. A method for removing an ostomy bag with a connector from an adapter at a stoma using the combination of claim 1, which comprises:
sliding a lid onto a tubular section of the adapter in a direction roughly perpendicular to the axis of a protruding section of the adapter,
closing a second opening in a second part of the connector,
unlocking the connector from the adapter, and
removing the adapter from a first opening in the connector.

14. The method according to claim 13 wherein the lid which is slid onto the protruding section of the adapter is a replacement lid which is stored in the connector and the old lid remains in the connector attached to the ostomy bag once the adapter is removed from the connector.

15. A method for exchanging the lid on an adapter at a stoma using the combination of claim 1, which comprises:
inserting the adapter into a first opening in a first part of the lid exchanger, and
sliding, with respect to the first part, a second part of the lid exchanger which is displaceably connected to the first part, thereby sliding the lid off the end of the adapter, and sliding a replacement lid onto the end of the adapter.

16. A combination comprising an ostomy bag and the combination of a connector and adapter according to claim 1.

17. The combination according to claim 1, wherein the mounting means of the adapter comprises grooves or ridges formed complementary to ridges or grooves respectively on the detachable lid, the grooves or ridges running perpendicular to the axis of the tubular section.

18. The combination according to claim 1, wherein the adapter is an implant.

19. The combination according to claim 1, wherein the detachable lid is arranged to be mounted onto and removed from the end of the protruding section of the adapter by sliding the lid substantially perpendicularly to the axis of the protruding section.

20. The combination according to claim 1, wherein the lid further comprises ridges or grooves which are formed complementary to grooves or ridges respectively on the adapter which run perpendicular to the axis of the protruding section of the adapter.

21. The combination according to claim 18, wherein the lid further comprises a first seal.

22. The combination according to claim 18, wherein the detachable lid is gas permeable.

23. The combination according to claim 18, wherein the lid further comprises an odor filter.

* * * * *

UNITED STATES PATENT AND TRADEMARK OFFICE
CERTIFICATE OF CORRECTION

PATENT NO. : 7,699,824 B2
APPLICATION NO. : 11/740783
DATED : April 20, 2010
INVENTOR(S) : Axelsson et al.

It is certified that error appears in the above-identified patent and that said Letters Patent is hereby corrected as shown below:

Column 10:
Line 25 (claim 12, line 5), after "opening in the connector," begin a new subparagraph with "locking the adapter to the"

Signed and Sealed this

First Day of June, 2010

David J. Kappos
*Director of the United States Patent and Trademark Office*